(12) United States Patent
Hanson

(10) Patent No.: US 6,607,552 B1
(45) Date of Patent: Aug. 19, 2003

(54) ROLLING SOCKS

(75) Inventor: Scott M. Hanson, Savage, MN (US)

(73) Assignee: SciMed Life Systems, Inc., Maple Grove, MN (US)

(*) Notice: Subject to any disclaimer, the term of this patent is extended or adjusted under 35 U.S.C. 154(b) by 217 days.

(21) Appl. No.: 09/664,268

(22) Filed: Sep. 18, 2000

(51) Int. Cl.[7] .................................................. A61F 2/06
(52) U.S. Cl. ...................................... 623/1.11; 623/1.12
(58) Field of Search ............................ 623/1.11–1.13, 623/1.23; 60/194, 198, 108; 604/103.07

(56) References Cited

U.S. PATENT DOCUMENTS

| | | | |
|---|---|---|---|
| 4,187,390 A | 2/1980 | Gore ........................ 174/102 |
| 4,877,661 A | 10/1989 | House et al. ............... 428/34.9 |
| 4,950,227 A | 8/1990 | Savin et al. .................... 604/8 |
| 5,108,416 A | 4/1992 | Ryan et al. .................. 606/194 |
| 5,403,341 A | 4/1995 | Solar ......................... 606/198 |
| 5,643,278 A | 7/1997 | Wijay ........................ 606/108 |
| 5,662,703 A | 9/1997 | Yurek et al. .................... 623/1 |
| 5,788,707 A | 8/1998 | Del Toro et al. ............ 606/108 |
| 5,810,871 A | 9/1998 | Tuckey et al. .............. 606/198 |
| 5,836,965 A | 11/1998 | Jendersee et al. ........... 606/198 |
| 5,843,116 A | 12/1998 | Crocker et al. ............. 606/192 |
| 5,935,135 A | 8/1999 | Bramfitt et al. ............. 606/198 |
| 5,944,726 A | 8/1999 | Blaeser et al. .............. 606/108 |
| 5,968,069 A | 10/1999 | Dusbabek et al. ........... 606/194 |
| 5,980,530 A | * 11/1999 | Willard et al. .............. 606/195 |
| 6,059,813 A | 5/2000 | Vrba et al. .................. 606/198 |
| 6,183,505 B1 | 2/2001 | Mohn, Jr. et al. ........... 623/1.11 |
| 6,280,412 B1 | * 8/2001 | Pederson et al. ......... 604/103.07 |
| 6,331,186 B1 | * 12/2001 | Wang et al. ................ 623/1.11 |
| 6,432,130 B1 | * 8/2002 | Hanson ...................... 623/1.11 |

OTHER PUBLICATIONS

U.S. patent application Ser. No. 09/407,836, Wang et al., filed Sep. 28, 1999.
U.S. patent application Ser. No. 09/664,267, F. Dicaprio et al., filed Sep. 18, 2000.
U.S. patent application Ser. No. 09/427,805, L. Wang et al., filed Oct. 27, 1999.
U.S. patent application Ser. No. 09/552,807, Scott Hanson, filed Apr. 20, 2000.
U.S. patent application Ser. No. 09/549,286, Gerberding et al., filed Apr. 14, 2000.

* cited by examiner

Primary Examiner—Michael J. Milano
Assistant Examiner—(Jackie) Tan-Uyen T. Ho
(74) Attorney, Agent, or Firm—Vidas, Arrett & Steinkraus P.A.

(57) ABSTRACT

A rolling retractable stent retaining sleeve for retaining a stent on a balloon catheter comprising a tubular sleeve. The tubular sleeve having a double walled construction which comprises an first layer and an second layer. A first portion of the first layer is constructed and arranged to engage at least a portion of a catheter. A second portion of the first layer is constructed and arranged to overlie an end of a stent prior to delivery of the stent. The first layer is everted such that it folds back upon itself to form the second layer. The double walled sleeve constructed and arranged to roll off of the stent during stent delivery.

40 Claims, 6 Drawing Sheets

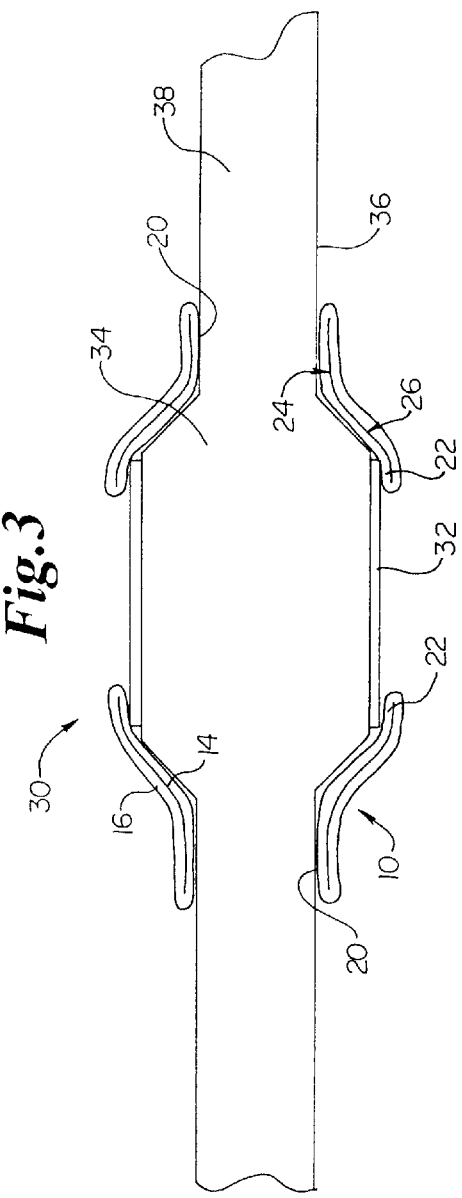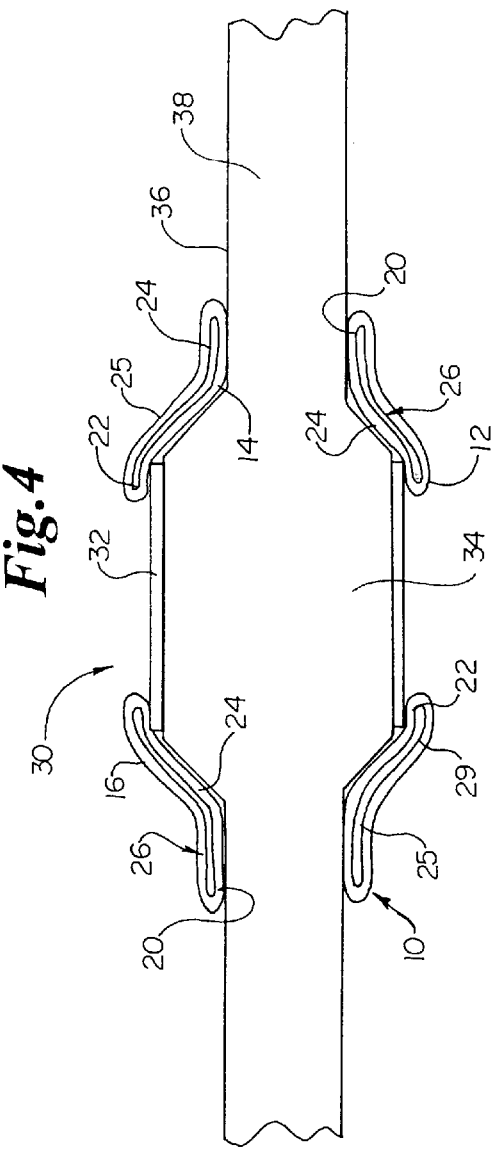

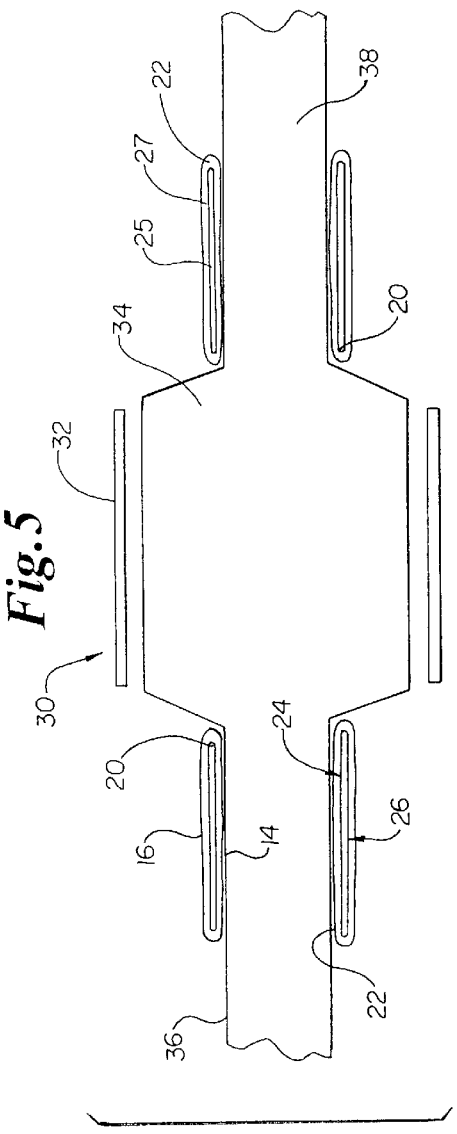

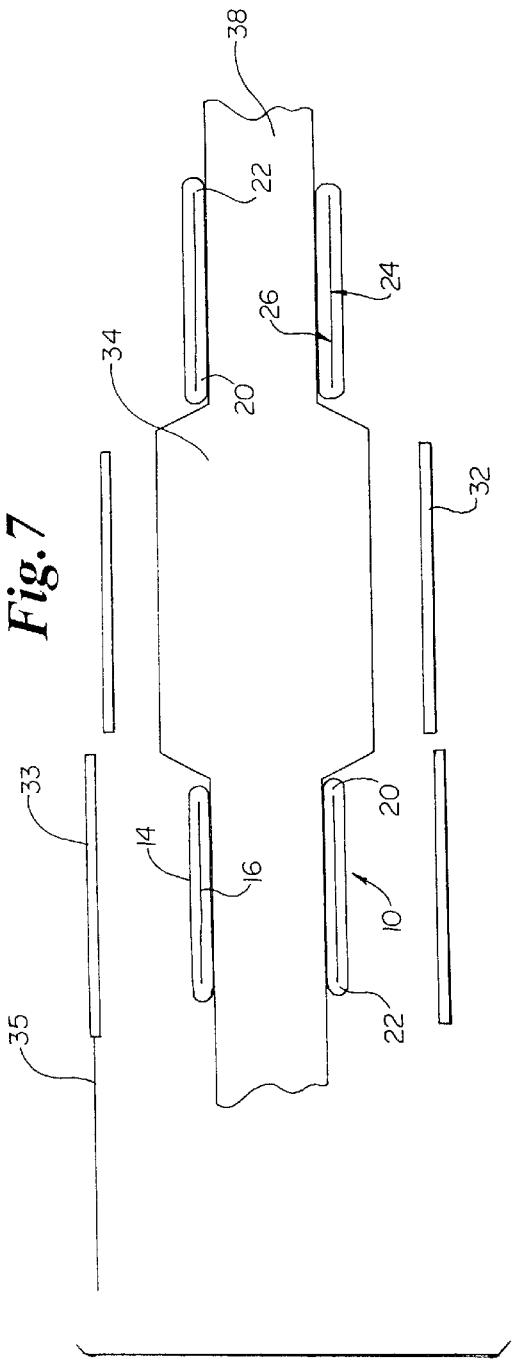
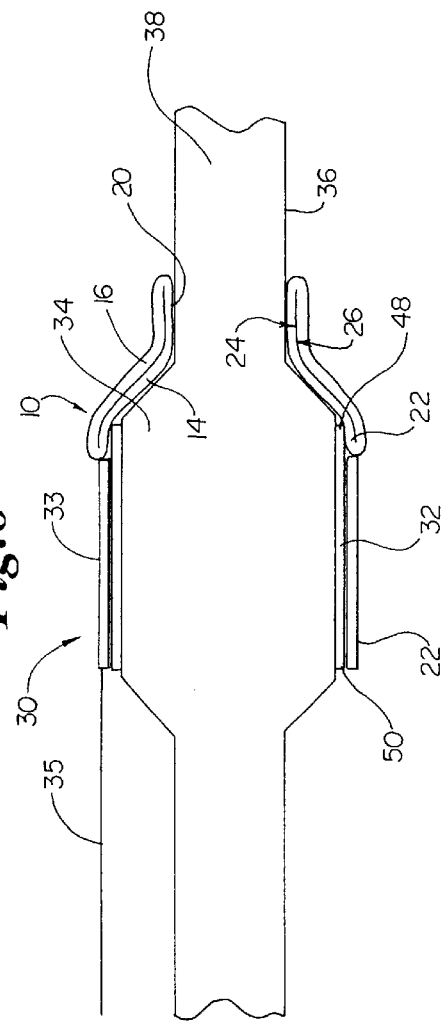

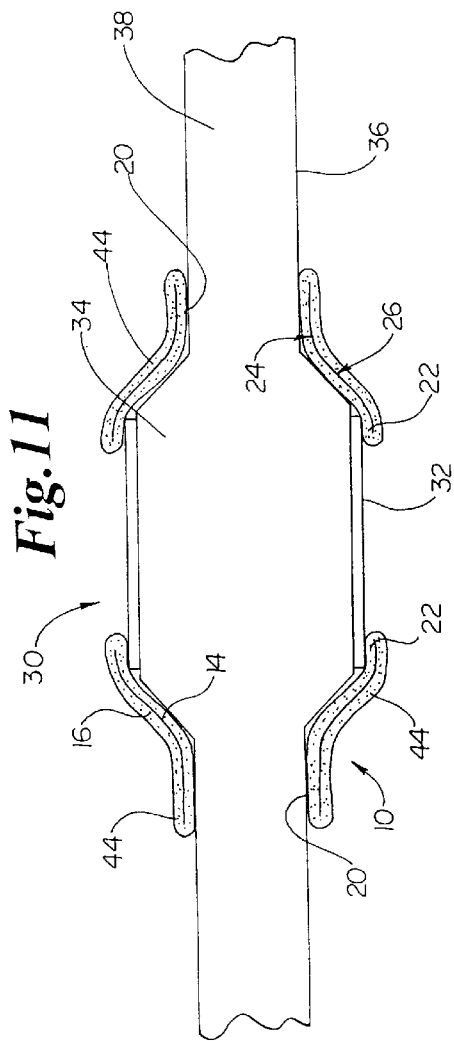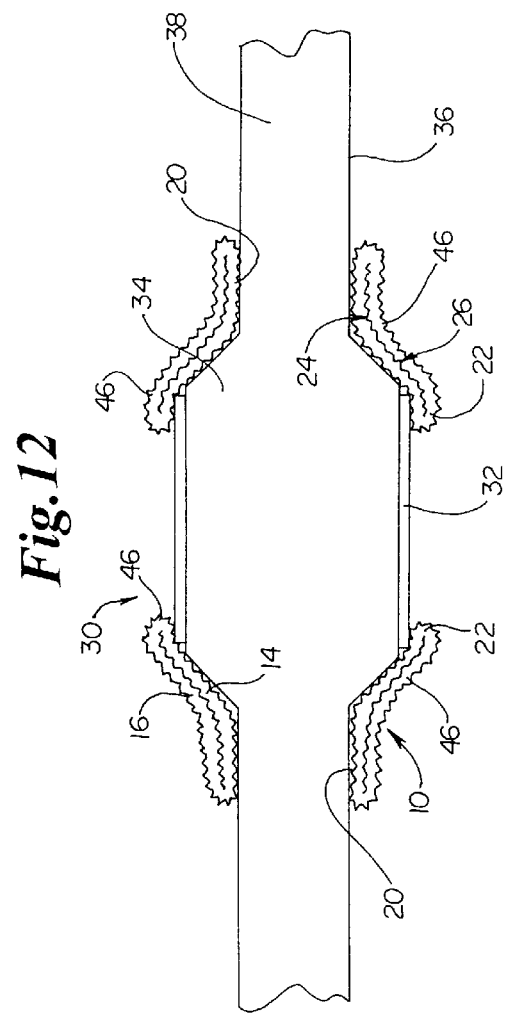

ROLLING SOCKS

CROSS-REFERENCE TO RELATED APPLICATIONS

Not Applicable

STATEMENT REGARDING FEDERALLY SPONSORED RESEARCH

Not Applicable

BACKGROUND OF THE INVENTION

1. Field Of The Invention

This invention relates to a medical device delivery systems, namely catheter mounted stent delivery systems. More particularly, the present invention is directed to socks or sleeves used to retain a stent on a stent delivery catheter. The present invention provides for one or more stent end retaining sleeves having a double wall construction. The double wall construction allows the sleeve(s) to be readily and completely retracted off the stent ends during a stent delivery procedure while retaining an extremely low profile relative to the catheter. In at least one embodiment of the invention the double wall sleeve(s) may be characterized as a tube folded over upon itself to form a continuous loop, wherein a portion of the folded over tube overlies an end of the stent and a portion of the tube is engaged to the catheter shaft. The tube may be retracted off of the stent in a number of ways. The tube may be constructed to roll, slide, or otherwise retract away from the stent when the stent expands during delivery. The sleeve may be used singly or in pairs with either self-expanding or balloon expandable stents. In the case of a self expanding stent, one or more sleeves may be utilized in conjunction with one or more retractable sheaths. The sleeve(s) may be provided in a variety of lengths to provide partial to full stent coverage. Other inventive aspects and embodiments of the present end retaining sleeves will be made apparent below.

2. Description Of The Related Art

Stents and stent delivery assemblies are utilized in a number of medical procedures and situations, and as such their structure and function are well known. A stent is a generally cylindrical prosthesis introduced via a catheter into a lumen of a body vessel in a configuration having a generally reduced diameter and then expanded to the diameter of the vessel. In its expanded configuration, the stent supports and reinforces the vessel walls while maintaining the vessel in an open, unobstructed condition.

Both self-expanding and inflation expandable stents are well known and widely available in a variety of designs and configurations. Self-expanding stents must be maintained under positive external pressure in order to maintain their reduced diameter configuration during delivery of the stent to its deployment site. Inflation expandable stents may be crimped to their reduced diameter about the delivery catheter, maneuvered to the deployment site, and expanded to the vessel diameter by fluid inflation of a balloon positioned on the delivery catheter. The present invention is particularly concerned with delivery and deployment of inflation expandable stents, although it is generally applicable to self-expanding stents when used with balloon catheters.

In advancing an inflation expandable stent through a body vessel to the deployment site, there are a number of important considerations. The stent must be able to securely maintain its axial position on the delivery catheter, without translocating proximally or distally, and especially without becoming separated from the catheter. The stent, particularly its distal and proximal ends, must be protected to prevent distortion of the stent and to prevent abrasion and/or reduce trauma of the vessel walls.

Inflation expandable stent delivery and deployment assemblies are known which utilize restraining means that overlie the stent during delivery. U.S. Pat. No. 4,950,227 to Savin et al, relates to an expandable stent delivery system in which a sleeve overlaps the distal or proximal margin (or both) of the stent during delivery. That patent discloses a stent delivery system in which a catheter carries, on its distal end portion, a stent which is held in place around the catheter prior to and during percutaneous delivery by means of one and preferably two sleeves. The sleeves are positioned around the catheter with one end portion attached thereto and overlap an end portion(s) of the stent to hold it in place on the catheter in a contracted condition. Each sleeve is elastomeric in nature so as to stretch and release the stent when it expands for implantation. The stent is expandable by means of the expandable balloon on the catheter. During expansion of the stent at the deployment site, the stent margins are freed of the protective sleeve(s). U.S. Pat. No. 5,403,341 to Solar, relates to a stent delivery and deployment assembly which uses retaining sheaths positioned about opposite ends of the compressed stent. The retaining sheaths of Solar are adapted to tear under pressure as the stent is radially expanded, thus releasing the stent from engagement with the sheaths. U.S. Pat. No. 5,108,416 to Ryan et al., describes a stent introducer system which uses one or two flexible end caps and an annular socket surrounding the balloon to position the stent during introduction to the deployment site.

Copending U.S. patent application Ser. No. 09/407,836 which was filed on Sep. 28, 1999 and entitled *Stent Securement Sleeves and Optional Coatings and Methods of Use*, and which is incorporated in its entirety herein by reference, also provides for a stent delivery system having sleeves. In 09/407,836 the sleeves may be made up of a combination of polytetrafluoroethylene (hereinafter PTFE) as well as one or more thermoplastic elastomers. Other references exist which disclose a variety of stent retaining sleeves.

The entire content of all patents and applications listed within the present patent application are incorporated herein by reference.

BRIEF SUMMARY OF THE INVENTION

This invention provides for one or more low profile double walled stent retaining sleeves which may be readily and fully retracted from a stent during stent delivery. The rolling retractable sleeves of the present invention improve over the prior art by providing a unique sleeve(s) which is designed to completely retract off of the stent during the stent delivery procedure. The present sleeve(s) are double-walled providing the sleeve(s) with the ability to roll and/or are otherwise retracted off of the stent ends by moving, such as by rolling, away from the stent mounting region or balloon along the catheter shaft. The ability of a sleeve to rollingly retract off of the stent allows the sleeve to retain its general shape and low profile throughout the stent delivery procedure.

In at least one embodiment of the invention the inside surfaces of the walls of the double walled sleeve may be lubricious in nature, have a lubricious coating thereon, or define a space which may contain a lubricant. The double walled structure of the sleeves allows each sleeve to be rollingly retracted completely off of a stent during stent delivery and avoids an accordion or wrinkled sleeve profile subsequent to stent delivery. The sleeves may be comprised of a combination of materials to provide the sleeves with a variety of characteristics such as those described in detail below.

BRIEF DESCRIPTION OF THE SEVERAL VIEWS OF THE DRAWINGS

A detailed description of the invention is hereafter described with specific reference being made to the drawings in which:

FIG. 3 is a side view of another embodiment of the invention;

FIG. 4 is a side view of another embodiment of the invention;

FIG. 5 is a side view of the embodiment shown in FIG. 4, shown subsequent to stent delivery;

FIG. 6 is a side view of another embodiment of the invention;

FIG. 7 is a side view of the embodiment shown in FIG. 6 wherein the protective sheath has been retracted;

FIG. 8 is a side view of another embodiment of the invention;

FIG. 11 is a side view of another embodiment of the invention; and

FIG. 12 is a side view of another embodiment of the invention.

DETAILED DESCRIPTION OF THE INVENTION

Figure 1:
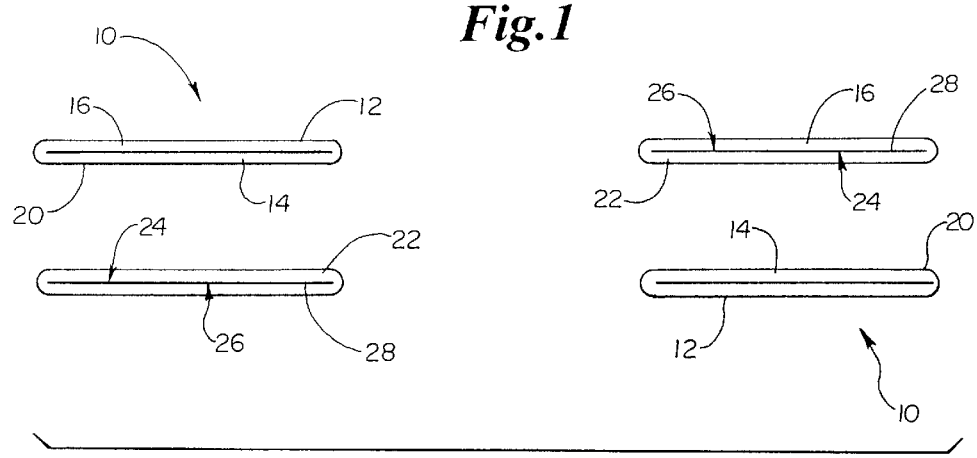
FIG. 1 is a side view of an embodiment of the invention.

As previously discussed, the present invention is directed to one or more double walled stent retaining sleeves. In FIG. I a pair of stent retaining sleeves, indicated generally at 10, are shown. The individual sleeves 10, are composed of a tubular double walled member 12. The double walled member 12 may be characterized as having a an inside layer 14 and an outside layer 16, wherein the inside layer 14 and the outside layer 16 are bonded together to be continuous with one another. The double walled member 12 is formed by folding or everting one of the layers, such as the inside layer 14, back upon itself to form the other layer, such as outside layer 16.

The double walled member 12 when utilized with the stent delivery system 30, such as may be seen in the embodiments shown in FIGS. 3–9, provides such the system 30 with stent retaining sleeves 10 which may be retracted completely off of the stent 32 during a stent delivery procedure. As may best be seen in FIG. 5, in at least one of the embodiments discussed herein, the double walled construction of the sleeves 10 provides the sleeves with the ability to roll off of the balloon or stent mounting region 34 of the catheter 36 during stent delivery.

The sleeves 10 may be constructed to rollingly retract when subjected to a predetermined outwardly acting force. In the case of a self-expanding stent, such as may be seen in FIGS. 6–9, when the sheath 33 is retracted off of the stent 32 by pulling the sheath 33 proximally via a pull back member 35, the stent 32 will exert an outwardly acting radial force against the sleeves 10. As may be seen in FIGS. 7 and 9, the force supplied by the stent 32 will cause the sleeve(s) 10 to retract off of the stent.

Figure 9:
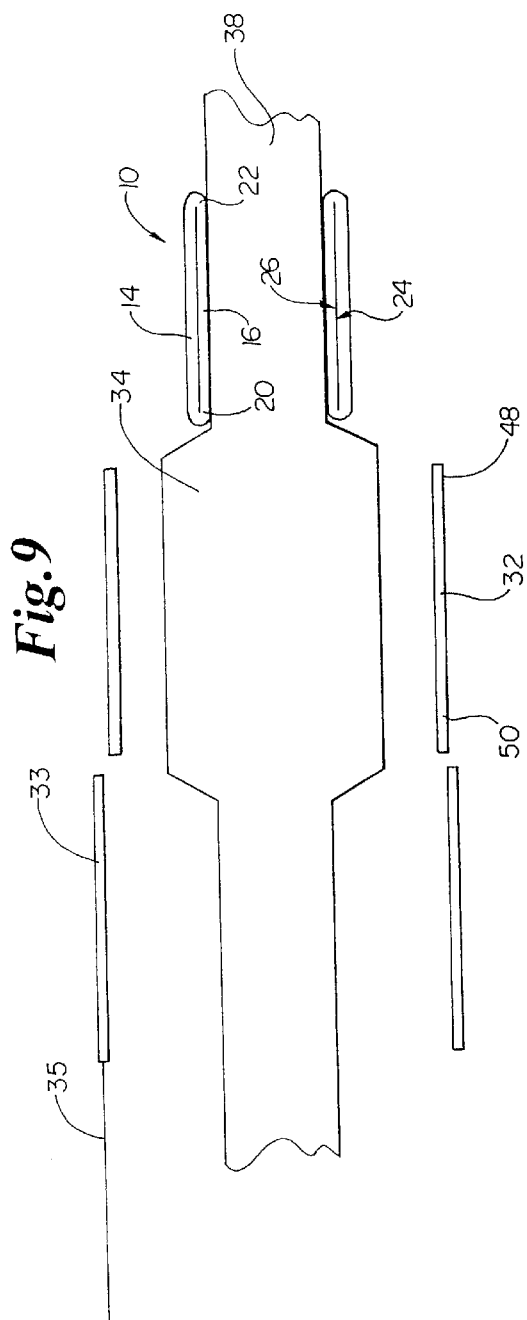
FIG. 9 is a side view of the embodiment shown in FIG. 8 wherein the protective sheath has been retracted.

In the embodiment shown in FIGS. 8 and 9 a single sleeve 10 is used to overlay only one end of the stent 32. As with any embodiment of the present invention, the sleeve 10 may be configured to have a wide variety of lengths so as to provide for a variable extent of stent coverage. The sleeve 10 may even extend over the length of the entire stent 32. However, in the embodiment shown, the sleeve 10 overlays the distal stent end 48 while the sheath 33 overlays the proximal end 50. When the sheath 33 is retracted via the pull back member 35 the proximal end 50 is released resulting in a momentary flaring of the proximal end 50 as the it begins to expand. As the proximal end 50 expands the sleeve 10 will retract off of the distal end 48 thereby allowing the distal end 48 to expand with the proximal end 50.

In the embodiments shown in FIGS. 6–9 the stent mounting region 34 may be an unexpanding portion of the catheter 36 or it may be expandable as previously discussed.

In an embodiment where the sleeves 10 are utilized with a balloon expandable stent 32, such as may be seen in the embodiments shown in FIGS. 3–5, the force supplied by the expanding balloon 34 which causes the stent 32 to expand, will likewise trigger the retraction of the sleeves 10 off of the stent 32. In the case of a balloon expandable stent, the force exerted by the balloon 34 will typically be 6 atmospheres or less.

Depending on several variables including: the materials used to make the sleeves, the materials used to make the catheter/balloon, and the type of engagement between the catheter and each sleeve; the sleeve(s) 10 may be configured to retract off of the stent 32 in a variety of manners.

The balloon 34 may be constructed of compliant materials, noncompliant materials or a combination thereof. The balloon 34 may be composed of compliant materials which include low pressure, relatively soft or flexible polymeric materials, such as thermoplastic polymers, thermoplastic elastomers, polyethylene (high density, low density, intermediate density, linear low density), various co-polymers and blends of polyethylene, ionomers, polyesters, polyurethanes, polycarbonates, polyamides, poly-vinyl chloride, acrylonitrile-butadiene-styrene copolymers, polyether-polyester copolymers, and polyether-polyamide copolymers. Other suitable materials include a copolymer polyolefin material available from E.I. DuPont de Nemours and Co. (Wilmington, Del.), under the trade name SURLYN™ Ionomer and a polyether block amide available under the trade name PEBAX™. Non-compliant materials include relatively rigid of stiff high pressure polymeric materials, such as thermoplastic polymers and thermoset polymeric materials, poly(ethylene terephthalate) (commonly referred to as PET), polyimide, thermoplastic polyimide, polyamides, polyesters, polycarbonates, polyphenylene sulfides, polypropylene and rigid polyurethanes.

Depending on the composition of the balloon 34 and the resulting extent of the frictional engagement between the balloon 34 and the sleeve 10, the sleeves 10 may be configured to roll, slide, "snap" off, or otherwise retract in any manner or combination of manners such as is know in the art. An additional benefit provided for by the sleeves 10 of the present invention, is that the sleeves 10 may be fully retracted from the stent 32 without "bunching up" or taking on an accordion-like configuration, which many prior sleeves are known to do. The present sleeves 10 may be provided with the ability to fully retract off of the stent 32 as well as the stent mounting region 34 while retaining the same sleeve profile throughout all phases of a stent delivery procedure.

In the present invention, the sleeves 10 are constructed such that a stent engagement end 22 of the double walled member 12 will tend to roll away from the stent 32 and stent mounting region 34, along the catheter shaft 38. As may be seen in FIG. 5, in at least one embodiment of the invention, the sleeves are capable of rolling along the catheter shaft 38, while retaining their general shape and profile, to fully retract off of the stent 32. In order to assure that sleeves 10 roll away from and off of the stent 32, a portion or end 20 of the inside layer 14 is constructed and arranged to engage a portion of a catheter shaft 38. In the various embodiments invention, the sleeve 10 may be utilized on a catheter 36, the catheter engagement end 20 may be engaged to a shaft 38 in a number of ways including but not limited to: frictional engagement; bonding, such as through the application of an adhesive; welding, such as heat, laser, and/or chemical welding.

In at least one embodiment of the invention, the sleeves my be configured to rollingly retract only partially off of the stent mounting region 34, or to rollingly retract varying distances from the stent 32 and/or stent mounting region 34 as may be desired by the user.

As may be seen in FIGS. 1 and 3, the sleeves of the present invention may be configured to have little or no space between the inside layer 14 and the outside layer 16. In the present embodiment, the layers 14 and 16 have surfaces 24 and 26 which are immediately adjacent to one another. One or both surfaces 24 and 26, or one or more portions thereof, may be lubricious or have a lubricious coating 28 thereon.

Figure 2:
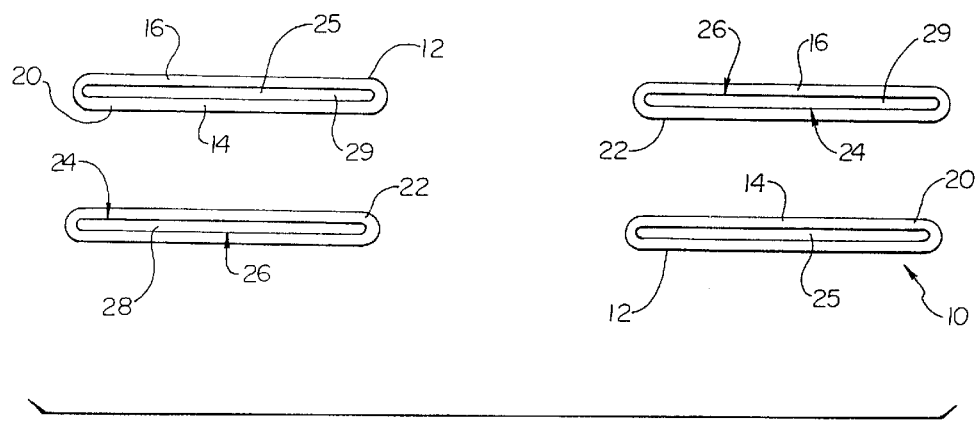
FIG. 2 is a side view of another embodiment of the invention.

Alternatively, in the various embodiments shown in FIGS. 2 and 4, the surfaces 24 and 26 may define a sealed space or chamber 25. The closed space 25 may be occupied in whole or in part by a lubricious material 29. The lubricious material 29 may be any material such as a fluid or a fluid like material which provides a reduced frictional engagement between the surfaces 24 and 26. The lubricious material or coating may be, but is not limited to, the following materials: silicones; PVP (polyvinyl pyrrolidone); PPO (polypropylene oxide); PEO; oils, such as mineral oil, olive oil, vegetable oil, or other natural oils; wax; BioSlide™, a biocompatable coating produced by SciMed (BioSlide™ is a hydrophilic, lubricious coating comprising polyethylene oxide and neopentyl glycol diacrylate polymerized in a solution of water and isopropyl alcohol in the presence of a photoinitiator such as azobisisobutronitrile); and any combination thereof.

In the embodiments shown in FIGS. 1 and 3, The need and/or effectiveness of a lubricious coating 28 may be dependant on the characteristics of the material used to construct the layers 14 and 16 and the interaction of the surfaces 24 and 26. As previously discussed, other factors may implicate the need and/or type of lubricant used, such as the interface between the catheter 34 and the sleeve 10. The layers 14 an 16 of sleeve 10 are typically manufactured from one or more thermoplastic elastomers, but may include additional and/or other materials as well. Some examples of suitable materials from which the layers 14 and 16 may be constructed include, but are not limited to: SURLYN™, PEBAX™ and urethane, polypropylene, low density polyethylene (LDPE), high density polyethylene (HDPE), ethylene vinyl acetate (EVA), nylon, polyester and polyethylene terephthalate ("PET"), and any combination thereof.

In addition to having a wide range of suitable materials which the sleeves 10 and the layers 14 and 16 thereof may be made from, the sleeves may include additional surface features. In FIG. 11 an embodiment of the invention is shown which incorporates holes 44. The holes 44 may be any of a variety of shapes and/or sizes and may be arranged either selectively or uniformly about the sleeve. Holes such as those utilized in the present embodiment are previously disclosed in U.S. patent application Ser. No. 09/549286, entitled *Stent Securement System*, filed Apr. 14, 2000, the entire content of which is incorporated herein by reference. The sleeves 10 may also include surface texture on any surface of the sleeve. In FIG. 12 an embodiment is shown which incorporates ribs 46. The sleeve 10 may be uniformly or selectively ribbed on any or all surfaces of the sleeve. A ribbed configuration is previously disclosed in U.S. patent application Ser. No. 09/552807, entitled A *Non-Crimped Stent Delivery System*, filed Apr. 20, 2000, the entire content of which is incorporated herein by reference.

The layers 14 and 16 may be constructed from the same or different materials. It may be desirable to provide a sleeve 10 which has a layer, be it the inside layer 14 or the outside layer 16 or a portion thereof, which has different characteristics than the other layer or portions. For example, for purposes of providing a sleeve 10 with increased columnar strength so as to better secure a stent in place prior to stent delivery, it may be desirable to construct one of the layers (14 or 16) or a portion thereof with a material which has more rigidity or greater hardness (as measured by the Shore scale) than the other layer which is less hard so as to promote flexibility. As indicated, the present invention also envisions sleeves which have only a portion or portions, such as the stent engagement end 22 and/or the catheter engagement end 20, having various and different material compositions. It should also be noted that end 22 may include a lubricious surface or coating as discussed herein.

Where the layers 14 and 16 are composed of a variety of materials, the materials which make up the layers 14 and 16 may be bonded together by any means known.

Figure 10:
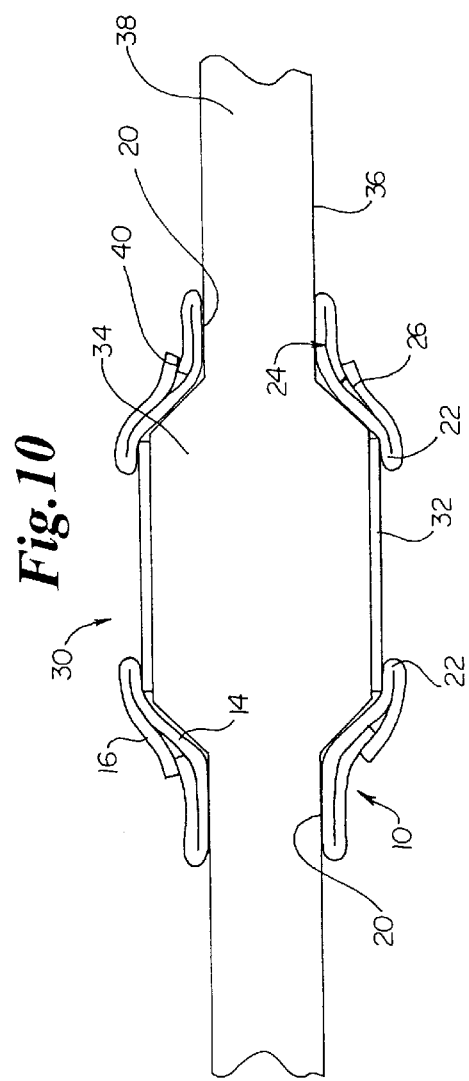
FIG. 10 is a side view of another embodiment of the invention.

Of particular concern to the present invention is the use of a lap weld to join the sleeve layers 14 and 16 together. A lap welded sleeve such as may be seen in FIG. 10, will provide sleeve 10 with a thickened portion 40. The thickened portion 40 provides the sleeve 10 with a natural fold or break point which will tend to draw the sleeve 10 away from the stent 32 during expansion, and which will also provide the sleeve 32 with a point upon which the sleeve 10 will tend to fold over upon itself, should the sleeve fail to roll away from the stent 32. Such folding action in prior sleeve designs is well known to those of skill in the art. Though the use of a lap weld is envisioned as a means to bond different compositional layers 14 and 16 together, the use of a thickened portion 40 may be used in any of the embodiments discussed herein. The addition of a thickened portion may be provided by lap welding layers 14 and 16 together. Alternatively, the sleeve 10 may be originally manufactured, such as by extrusion with such a thickened portion 40 included.

In any of the embodiments discussed herein, a lubricious coating may be applied to any and all of the surfaces of the sleeve 10. The use of a lubricious material or coating 28 as previously discussed, may be avoided if the surfaces 24 and 26 have a frictional engagement such that the surfaces may readily slide against one another. If the surfaces 24 and 26 are chemically attracted to one another or tend to engage or otherwise interfere with the movement of one another as the sleeve 10 rolls, then the sleeve will not function properly. If it is not desired to lubricate the surfaces 24 and 26, the surfaces, or a portion or portions thereof, may be treated so that they behave in a lubricious manner. To make the surfaces 24 and 26 more lubricious, the surfaces or a portion or portions thereof may be treated to encourage cross-linking of the material from which the layers 14 and 16, and thus surfaces 24 and 26 are constructed from. Such cross-linking may be achieved by exposing the surfaces 24 and 26 to a plasma or charged ion field prior to mounting the sleeves on to the catheter 36.

The present invention is also directed to the use of other methods of encouraging or creating a lubricious surface on any of the layers 14 and 16, surfaces 24 and 26, and/or ends 20 and 22 as discussed above, which may be known in the art.

In addition to being directed to the embodiments described above and claimed below, the present invention is further directed to embodiments having different combinations of the features described above and claimed below. As such, the invention is also directed to other embodiments having any other possible combination of the dependent features claimed below.

The above examples and disclosure are intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is:

1. A stent delivery system comprising:
   a stent delivery catheter, the stent delivery catheter having a stent retaining region;
   a stent disposed about at least a portion of the stent retaining region, the stent having an unexpanded state and being expandable to an expanded state;
   at least one stent retaining sleeve, the at least one sleeve having a tubular double walled construction comprising a first layer and a second layer, a lubricant between the first layer and the second layer, a first portion of the first layer engaging at least a portion of the stent delivery catheter, a second portion of the first layer overlying an end of the stent when the stent is in the unexpanded state, the at least one stent retaining sleeve constructed and arranged to rollingly retract off of the stent when the stent is expanded to the expanded state, whereby during expansion of the stent the at least one sleeve retracts off of the stent.

2. The stent delivery system of claim 1, comprising a pair of sleeves.

3. The stent delivery system of claim 2, the first layer comprising an inside surface and the second layer comprising an inside surface.

4. The stent delivery system of claim 3, wherein at least a portion of the inside surface of the first layer is in sliding contact with at least a portion of the inside surface of the second layer.

5. The stent delivery system of claim 4 wherein the at least a portion of the inside surface of the first layer and the at least a portion of the inside surface of the second layer material are composed substantially of cross-linked materials.

6. The stent delivery system of claim 5, wherein the cross-linked materials are produced by exposing the at least a portion of the inside surfaces of the first and second layers to a plasma field.

7. The stent delivery system of claim 3, wherein the inside surface of the first layer and the inside surface of the second layer define a closed space therebetween.

8. The stent delivery system of claim 7, wherein the closed space is at least partially filled with the lubricant.

9. The stent delivery system of claim 8, wherein the lubricant is selected from the group consisting of: silicones, polyvinyl pyrrolidone, polypropylene oxide, mineral oil, olive oil, vegetable oil, wax, compounds of polyethylene oxide and neopentyl glycol diacrylate polymerized in a solution of water and isopropyl alcohol in the presence of a photoinitiator, and any combination thereof.

10. The stent delivery system of claim 1, wherein the first layer is composed of a first material and the second layer is composed of a second material.

11. The stent delivery system of claim 10, wherein the first material is different from the second material.

12. The stent delivery system of claim 10, wherein the first material and the second material are each selected from the group consisting of: copolymer polyolefin, Ionomer and a polyether block amide, urethanes, polypropylene, low density polyethylene, high density polyethylene, ethylene vinyl acetate, nylon, polyester and polyethylene terephthalate, polyurethane, and any combination thereof.

13. The stent delivery system of claim 10, wherein the first layer is lap welded to the second layer.

14. The stent delivery system of claim 10, wherein the first layer and the second layer further comprise a thickened portion.

15. The stent delivery system of claim 11, wherein the second material has different Shore D hardness than the first material.

16. The stent delivery system of claim 1, wherein the stent delivery catheter further comprises a catheter shaft, the catheter shaft being adjacent to the stent retaining region, the first portion of the first layer being fixedly engaged to at least a portion of the catheter shaft.

17. The stent delivery system of claim 16, wherein the first portion of the first layer being welded to the at least a portion of the catheter shaft.

18. The stent delivery system of claim 16, wherein the first portion of the first layer being laser welded to the at least a portion of the catheter shaft.

19. The stent delivery system of claim 16, wherein the first portion of the first layer being adhesively bonded to the at least a portion of the catheter shaft.

20. The stent delivery system of claim 1, wherein the second portion of the first layer is lubricious.

21. The stent delivery system of claim 1 wherein the second portion of the first layer has a lubricious coating thereon.

22. The stent delivery system of claim 1, further comprising a retractable sheath, the retractable sheath having a proximally extending pull back member, the retractable sheath at least partially overlapping the stent prior to stent delivery.

23. The stent delivery system of claim 22, wherein the stent is a self-expanding stent.

24. The stent delivery system of claim 23, the retractable sheath overlapping a proximal portion of the stent prior to stent delivery.

25. The stent delivery system of claim 23, the at least one stent retaining sleeve overlapping at least a distal portion of the stent prior to stent delivery.

26. The stent delivery system of claim 2, further comprising a retractable sheath, the retractable sheath having a proximally extending pull back member, the retractable sheath overlapping the stent and the pair of stent retaining sleeves prior to stent delivery.

27. The stent delivery system of claim 1, the at least one stent retaining sleeve having at least one surface which is textured.

28. The stent delivery system of claim 27, wherein the at least one textured surface is ribbed.

29. The stent delivery system of claim 1, the first layer defining at least one hole therethrough.

30. The stent delivery system of claim 1, the second layer defining at least one hole therethrough.

31. The stent delivery system of claim 1, the first layer and the second each defining at least one hole therethrough.

32. The stent delivery system of claim 31, wherein the stent is balloon expandable.

33. The stent delivery system of claim 31, the stent retaining region comprising a stent delivery balloon.

34. The stent delivery system of claim 23, the stent retaining region comprising a stent delivery balloon.

35. A rolling retractable stent retaining sleeve for retaining a stent on a balloon catheter comprising:

a tubular double walled sleeve, the tubular double walled sleeve comprising a first layer and a second layer, a lubricant between the first layer of material and the second layer of material, a first portion of the first layer constructed and arranged to engage at least a portion of the balloon catheter, a second portion of the first layer constructed and arranged to overlay an end of the stent prior to stent delivery, the tubular double walled sleeve constructed and arranged to rollingly retract off of the stent when the stent exerts an outwardly acting radial pressure on the first portion, whereby during stent delivery the tubular double walled sleeve is fully retracted off of the stent.

36. The stent retaining sleeve of claim 35 wherein the sleeve further comprises a lubricant between the first layer of material and the second layer of material.

37. The stent retaining sleeve of claim 35 wherein the first layer and the second layer define a closed chamber.

38. The stent delivery system of claim 37 wherein the lubricant is contained in the closed chamber.

39. The stent delivery system of claim 35, at least a portion of the first portion having a lubricious coating thereon.

40. A method of delivering a stent comprising the steps of:

providing a stent delivery catheter wherein the stent delivery catheter includes characterized as having:
an inflatable region,
an expandable stent disposed about the inflatable region, the stent having an unexpanded state and an expanded state, and at least one tubular double walled sleeve, the at least one tubular double walled sleeve comprising a first layer and a second layer, a lubricant between the first layer of material and the second layer of material, a first portion of the first layer constructed and arranged to engage at least a portion of the catheter, a second portion of the first layer constructed and arranged to overlay an end of the stent prior to stent delivery, the at least one tubular double walled sleeve constructed and arranged to rollingly retract off of the stent when the stent is expanded to the expanded state, whereby during stent delivery the at least one tubular double walled sleeve is fully retracted off of the stent;

inserting the stent delivery catheter into a body vessel;

advancing the balloon catheter to a predetermined delivery location;

inflating the inflatable portion thereby expanding the stent from the unexpanded state to the expanded state and rollingly retracting the at least one sleeve off of the at least a portion of the stent thereby exposing the stent for delivery; and retracting the stent delivery catheter from the body vessel.

* * * * *